(12) United States Patent
Hauck et al.

(10) Patent No.: US 7,267,765 B2
(45) Date of Patent: Sep. 11, 2007

(54) PROTECTION OF THE CHROMATOGRAPHIC BED IN DYNAMIC AXIAL COMPRESSION CHROMATOGRAPHY DEVICES

(75) Inventors: Wilhelm Hauck, Wallingford, PA (US); Harlene Marks, Wallingfort, PA (US); Jean Blehaut, Bryn Mawr, PA (US); Roger Marc Nicoud, Lay-Saint-Christophe (FR)

(73) Assignee: Novasep, Pompey (FR)

( * ) Notice: Subject to any disclaimer, the term of this patent is extended or adjusted under 35 U.S.C. 154(b) by 456 days.

(21) Appl. No.: 11/010,258

(22) Filed: Dec. 14, 2004

(65) Prior Publication Data

US 2005/0087494 A1    Apr. 28, 2005

Related U.S. Application Data

(62) Division of application No. 10/366,689, filed on Feb. 14, 2003, now Pat. No. 6,843,918.

(30) Foreign Application Priority Data

Feb. 15, 2002    (FR) .................................. 02 01911

(51) Int. Cl.
*B01D 15/08*    (2006.01)
(52) U.S. Cl. .................................... 210/198.2; 210/656
(58) Field of Classification Search ............... 210/635, 210/656, 657, 659, 198.2, 238, 232; 141/12, 141/73, 80
See application file for complete search history.

(56) References Cited

U.S. PATENT DOCUMENTS

| | | | |
|---|---|---|---|
| 3,966,609 A | 6/1976 | Godbille et al. | 210/198.2 |
| 4,597,866 A | 7/1986 | Couillard | 210/198.2 |
| 5,234,587 A * | 8/1993 | Allington et al. | 210/198.2 |
| 5,242,586 A | 9/1993 | Ransohoff | 210/198.2 |
| 5,641,893 A | 6/1997 | Penn et al. | 73/61.53 |
| 6,019,897 A * | 2/2000 | Horsman et al. | 210/198.2 |
| 6,099,724 A * | 8/2000 | Dourdeville | 210/198.2 |

* cited by examiner

*Primary Examiner*—Ernest G. Therkorn
(74) *Attorney, Agent, or Firm*—Millen, White, Zelano & Branigan, P.C.

(57) ABSTRACT

The invention relates to a chromatography device comprising:
  a column (12) intended to house, between its two ends (16a, 16b) a chromatographic bed (14) and a fluid to be chromatographed, a fluid layer (48) being defined between a surface of the bed (14) and one (16a) of the ends of the column (12);
  a piston (36) sliding in the column (12), the piston (36) being one of the ends (16a, 16b) of the column (12);
  at least a first probe (45, 46) for detecting the surface of the bed (14), the probe (45, 46) being mounted on the end (16a) of the column (12) defining the layer (48); and
  means (52) for adjusting the position of the piston (36) according to the detection of the surface of the bed (14) by the probe (45, 46).

The invention also relates to processes for separating at least two compounds of a fluid to be chromatographed and to methods of adjusting the position of the piston with respect to the surface of the chromatographic bed using the chromatography device.

The invention has the advantage of allowing effective separation of the compounds of the fluid to be chromatographed while ensuring that the bed is protected.

13 Claims, 3 Drawing Sheets

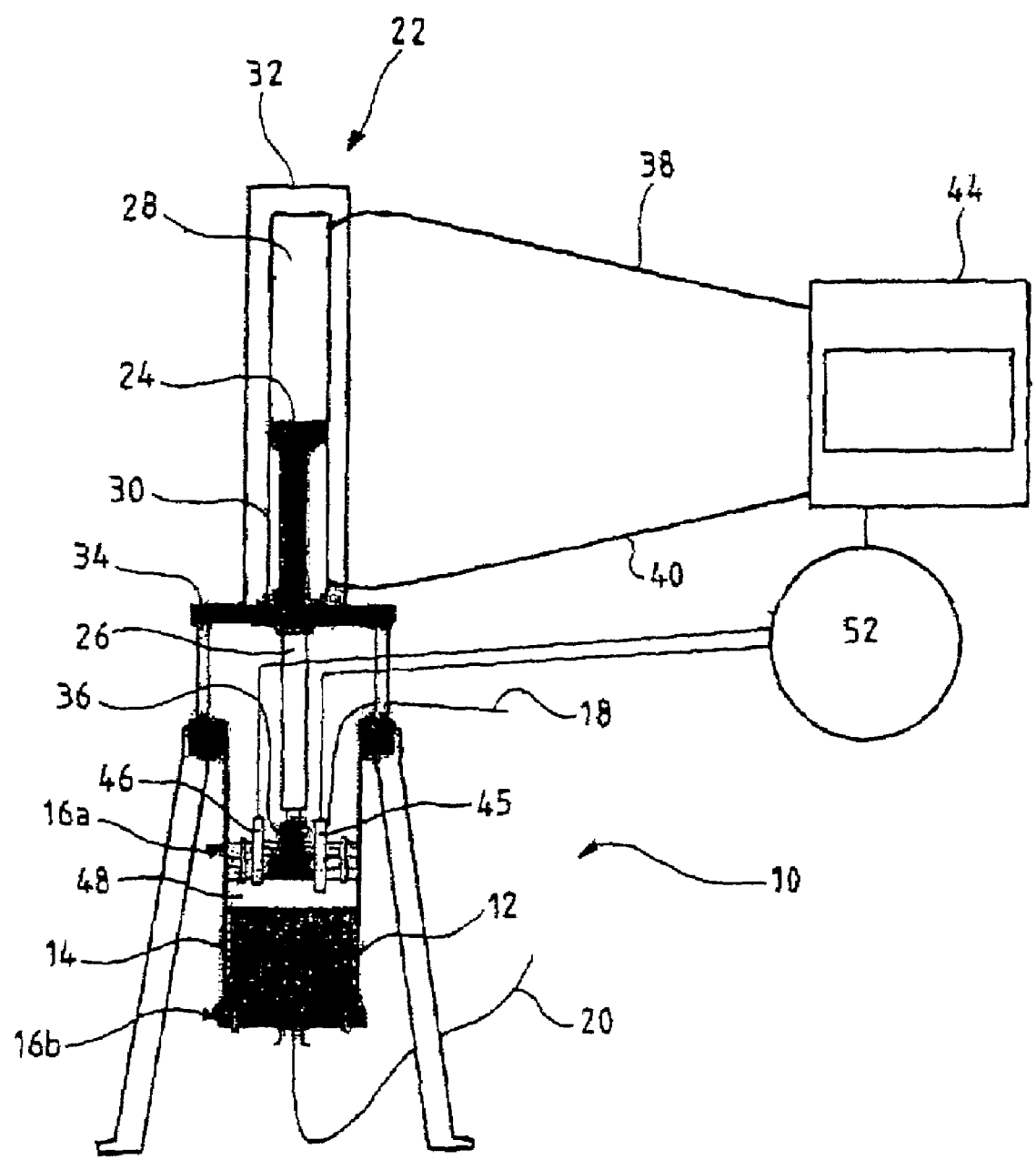
FIG_1

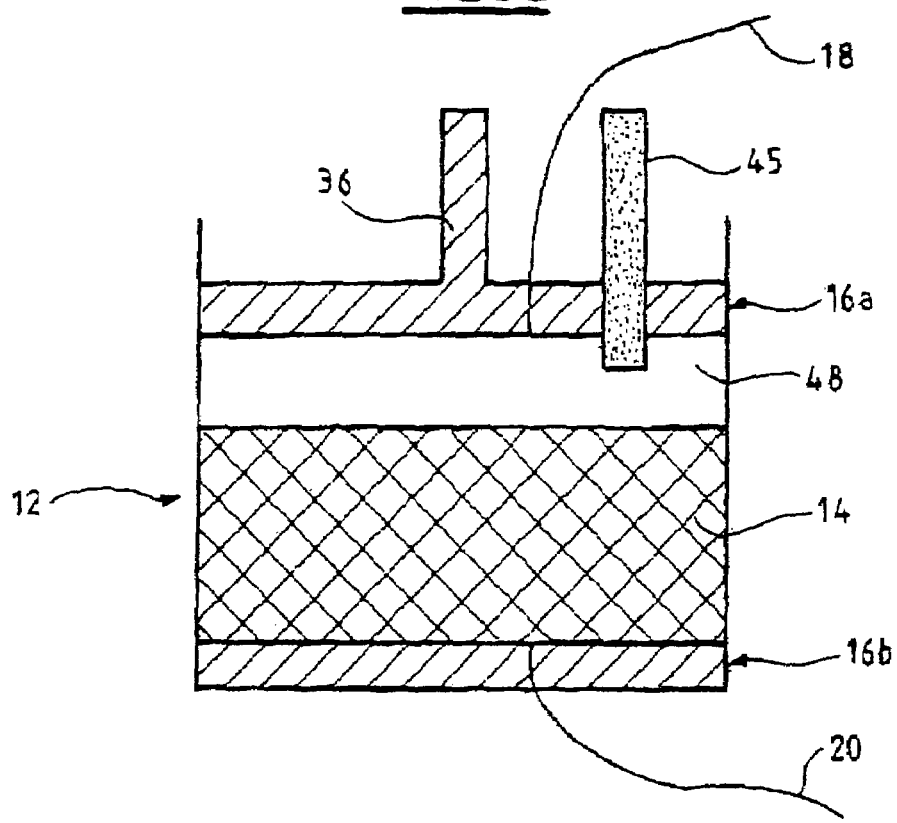
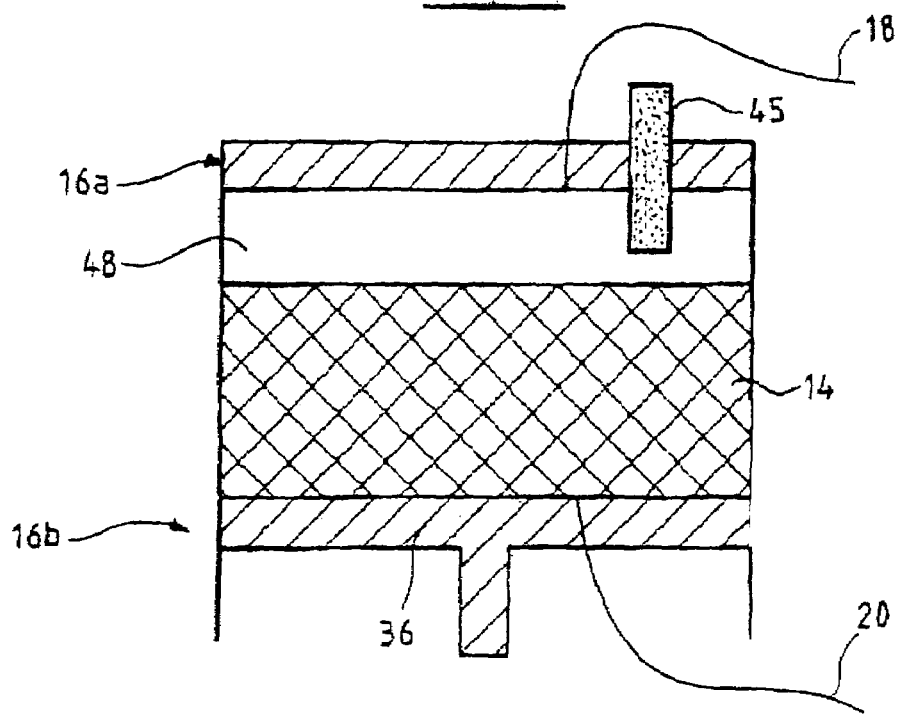

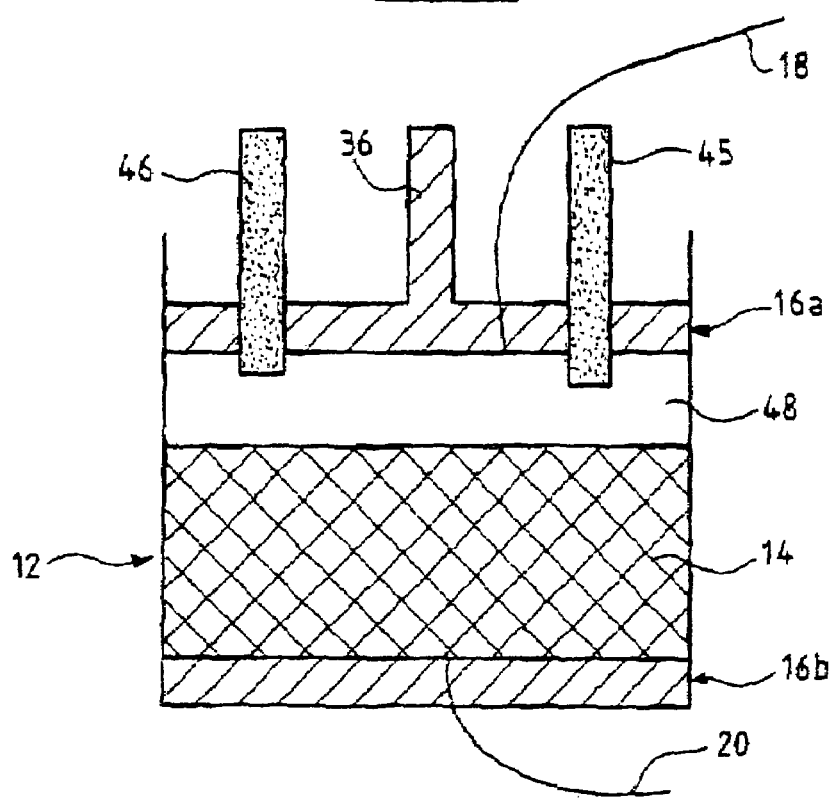
FIG_4
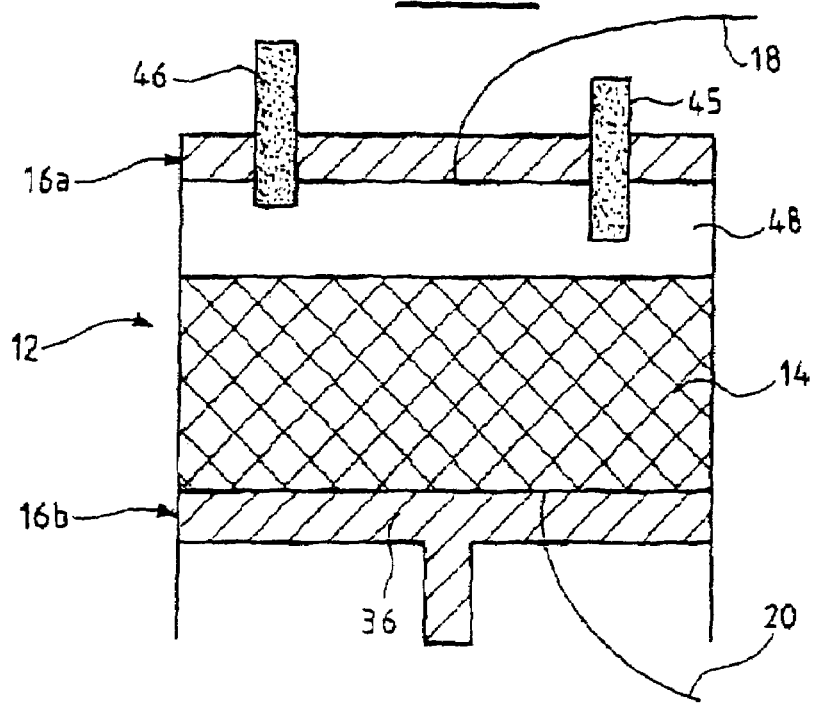
FIG_5

PROTECTION OF THE CHROMATOGRAPHIC BED IN DYNAMIC AXIAL COMPRESSION CHROMATOGRAPHY DEVICES

RELATED APPLICATIONS

This application is a division of application Ser. No. 10/366,689, filed Feb. 14, 2003, now U.S. Pat. No. 6,843,918.

FIELD OF THE INVENTION

The present invention relates to the protection of the chromatographic bed in chromatography devices and in particular in dynamic axial compression devices.

TECHNOLOGICAL BACKGROUND

In a chromatography separation process, the effectiveness of the column used is a key parameter. The column is generally filled with a solid product in the form of very fine particles usually having a size within 5 and 100 µm, forming the chromatographic bed. To obtain high effectiveness, the arrangement of the particles inside the column must be as uniform as possible, and empty spaces between the chromatographic bed and the inlet/outlet parts of the column must be avoided. It is known from the prior art to use DAC (Dynamic Axial Compression) columns to ensure that there is a compact bed with no free space between the inlet/outlet distributors and the bed.

Dynamic axial compression columns have a piston or another sliding body driven by a cylinder, actuated, for example, by an independent hydraulic circuit; the sliding body makes it possible to compact the packing in a chamber between this piston and a fixed bottom or removable cover. The sliding body comes into contact with the solid phase so as to maintain a constant mechanical pressure on the bed.

Thus, French Patent Application FR-A-2 219 797 teaches a chromatography apparatus in the form of a column designed to contain a bed of adsorbent material. The apparatus consists of a tube which includes a cover and a body sliding in the tube allowing pressure to be exerted in the tube. The sliding body is a piston having at its head a fluid-permeable porous plate. To obtain the bed intended for chromatography, a suspension of particles of a material capable of constituting an adsorbent bed is introduced into the tube without its cover. The cover is fitted to the tube and then pressure is exerted on the said suspension by means of the piston. The liquid is driven through the porous plates and the said particles are compressed between the piston and the cover. This apparatus makes it possible to achieve, in one embodiment, the chosen bed compression stage and the desired particle compaction when the sliding body has travelled between ⅖ and ⅔ of the height of the column.

However, this apparatus has the drawback of achieving imprecise compaction of the bed, since this is determined simply by the position of the piston along the tube. Moreover, there is a risk of the pressure exerted by the piston being greater than the mechanical stresses that the bed can withstand and contact between the bed and the piston may cause the bed to degrade. Furthermore, this apparatus does not make it possible to take into account the risk of the piston crushing the bed, which may degrade the latter.

European Patent Application EP-A-0 145 578 also discloses a chromatography apparatus comprising a tube, one portion of which is intended to contain an adsorbent bed. This tube has two end walls and a piston sliding longitudinally in the tube. The piston marks, between the two end walls, a separation between a chromatography chamber containing the bed and a enclosure in which pressure is applied so as to displace the piston along the tube. The particular feature of that device is that the fluid contained in the enclosure is the liquid to be chromatographed, diverted from the liquid feed line. One portion of the liquid is diverted to the enclosure via an enclosure line and the other portion of the liquid is carried to the chromatography chamber via a flow line passing through the enclosure and the piston. Once the piston is in equilibrium, the force exerted on the enclosure side on the piston is equal to the sum of the force on the piston caused by the flow in the chamber of the liquid to be chromatographed and of the mechanical force of the bed on the piston.

This apparatus makes it possible, in addition to carrying out the elution step, to define the pressure exerted on the bed.

In a first embodiment, the piston has a constant cross section but the pressure in the flow and enclosure lines is regulated by pressure regulator stops. Thus, the stops may be set so that the difference between the pressure exerted by the flow of the liquid and the pressure exerted by the liquid in the enclosure is adjusted to a setpoint pressure on the bed.

In another embodiment, the pressure in the flow and enclosure lines is the same, but the cross section of the piston differs. The piston is one having two cross sections and it slides in corresponding bores, the smaller cross section A being located on the chromatography chamber side and the larger cross section B on the enclosure side. Because of the difference in area of the faces A and B of the piston, the force exerted at B is greater than the force exerted at A. Thus, it is possible to choose the cross sections of the piston so that the difference between the pressure exerted by the flow of the liquid and the pressure exerted by the liquid in the enclosure is adjusted to a setpoint pressure on the bed.

In fact, the apparatus described in the above document has various drawbacks. It does not make it possible to know the position of the piston along the tube, which may crush the bed. This is particularly serious when there is a risk of the chromatographic bed being mechanically degraded. In addition, since the movements of the chromatographic bed are not monitored and the enclosure is unable to discharge the liquid, this apparatus cannot adapt the pressure exerted on the bed according to the movements of the latter and contact between the bed and the piston may degrade the bed. Moreover, this system cannot be used in SMB (Simulating Moving Bed) or in VARICOL mode. In such configurations, the chromatography apparatuses are mounted in a loop and the liquids injected into the beds alternate. In the apparatus disclosed in EP-A-0 145 578, the same liquid is sent into the bed and into the enclosure, the alternating injection of liquids causing the latter to be mixed.

SUMMARY OF THE INVENTION

The subject of the invention is a chromatography device in which the effectiveness of the column is improved, while ensuring that the chromatographic bed is protected.

The invention relates to a chromatography device comprising:

a column intended to house, between its two ends, a chromatographic bed and a fluid to be chromatographed, a fluid layer being defined between a surface of the bed and one of the ends of the column;

a piston sliding in the column, the piston being one of the ends of the column;

at least a first probe for detecting the surface of the bed, the probe being mounted on the end of the column defining the layer; and means for adjusting the position of the piston according to the detection of the surface of the bed by the probe.

The probe may be fixed on the end. Alternatively, the probe may be capable of undergoing oscillatory movements with respect to the end.

Typically the probe projects into the layer. The probe may be a capacitive probe.

The device may furthermore include a second probe for detecting the surface of the bed, the second probe being mounted on the end of the column defining the layer. Preferably, the first probe projects further into the layer than the second probe.

The invention also relates to a combination of chromatography devices as described above within the context of the invention, in which the devices are looped together.

The invention also relates to the following separation processes and adjustment methods:

a process for separating at least two compounds of a fluid to be chromatographed, comprising the chromatography of the said fluid in the device as described above within the context of the invention, the process comprising the following steps:

flow of the liquid to be chromatographed through the bed; and collection of the chromatographed fluid;

a process for separating at least two compounds of a fluid to be chromatographed, comprising the chromatography of the said fluid in the device described above within the context of the invention with one probe, the piston being the end defining the layer and the process comprising the following steps:

flow of the fluid to be chromatographed through the bed;

raising of the piston when the probe detects the surface of the bed;

lowering of the piston when the probe no longer detects the surface of the bed; and collection of the chromatographed fluid;

a process for separating at least two compounds of a fluid to be chromatographed, comprising the chromatography of the said fluid in the device described above within the context of the invention with one probe, the piston being the lower end of the column and the process comprising the following steps:

flow of the liquid to be chromatographed through the bed;

lowering of the piston when the probe detects the surface of the bed;

raising of the piston when the probe no longer detects the surface of the bed; and collection of the chromatographed fluid;

a process for separating at least two compounds of a fluid to be chromatographed, comprising the chromatography of the said fluid in the device described above within the context of the invention with two probes, the piston being the end defining the layer and the process comprising the following steps:

flow of the liquid to be chromatographed through the bed;

raising of the piston when the probes detect the surface of the bed;

lowering of the piston when neither probe detects the surface of the bed; and collection of the chromatographed fluid;

a process for separating at least two compounds of a fluid to be chromatographed comprising the chromatography of the said fluid in the device described above within the context of the invention with two probes, the piston being the lower end of the column and the process comprising the following steps:

flow of the fluid to be chromatographed through the bed;

lowering of the piston when the probes detect the surface of the bed;

raising of the piston when neither probe detects the surface of the bed; and collection of the chromatographed fluid;

a method of adjusting the position of the piston in the device described above within the context of the invention with one probe, the piston being the end defining the layer and the method comprising the following steps:

raising of the piston when the probe detects the surface of the bed; and lowering of the piston when the probe no longer detects the surface of the bed;

a method of adjusting the position of the piston in the device described above within the context of the invention with one probe, the piston being the lower end of the column and the method comprising the following steps:

lowering of the piston when the probe detects the surface of the bed; and raising of the piston when the probe no longer detects the surface of the bed;

the above methods of adjustment in the device with one probe may furthermore include the step of oscillating the probe;

a method of adjusting the position of the piston in the device described above within the context of the invention with two probes, the piston being the end defining the layer and the method comprising the following steps:

raising of the piston when the probes detect the surface of the bed; and lowering of the piston when neither probe detects the surface of the bed;

a method of adjusting the position of the piston in the device described above within the context of the invention with two probes, the piston being the lower end of the column and the method comprising the following steps:

lowering of the piston when the probes detect the surface of the bed; and raising of the piston when neither probe detects the surface of the bed.

The device of the invention allows the use of chromatographic beds which are sensitive to pressure and which, in particular, do not allow the piston of the column to come into contact with them. The device makes it possible to maintain a gap between the piston and the surface of the bed. To do this, the device adapts the position of the piston according to the surface of the bed, while limiting the space above the bed and thus limiting the dispersion in order to maintain the effectiveness of the bed. Finally, the device allows effective separation of the compounds of the fluid to be chromatographed while ensuring that the bed is protected.

BRIEF DESCRIPTION OF THE DRAWINGS

Further features and advantages of the invention will become apparent on reading the following detailed description of the embodiments of the invention, these being given solely by way of example and with reference to the drawings which show:

FIG. 1, a chromatography device according to the invention; and

FIGS. 2 to 5, embodiments of the device of FIG. 1.

DESCRIPTION OF THE INVENTION

The device described below allows the chromatography of a fluid to be carried out.

The chromatography device 10 comprises a column 12 with an upper end 16a and a lower end 16b. The column 12 is intended to house, between its two ends 16a, 16b, a chromatographic bed 14 and the fluid to be chromatographed. The end 16a of the column 12 and a surface of the bed 14 define a fluid layer 48. A piston 36 slides in the column 12. The piston 36 is one of the ends 16a, 16b of the column 12. The device furthermore includes at least a first probe 45 for detecting the surface of the bed 14. The probe 45 is mounted on the end 16a of the column 12 defining the layer 48. The device also includes means 52 for adjusting the position of the piston 36 according to the detection of the surface of the bed 14 by the probe 45.

FIG. 1 shows schematically the chromatography device 10.

The chromatographic bed 14 rests on the lower end 16b of the column 12. The bed 14 used is, for example, gel for biochromatography, ion-exchange resins or polymer-based chiral phases. Depending on the type of bed used, the maximum stresses withstood are, for example, from 1 to 3 bar.

The fluid to be chromatographed enters the column 12 via one of the ends 16a, 16b and emerges via the other end. The fluid is conducted into and collected from the column 12 via respective lines 18, 20, or vice versa.

The piston 36 is one or other of the ends 16a, 16b of the column 12. When the piston 36 is the upper end 16a of the column 12 (FIG. 1), it forms the cover of the column 12 and the lower end 16b is the bottom of the column 12. The bed 14 rests on the bottom of the column and the piston 36 can slide so as to move closer to or further away from the upper surface of the bed. When the piston 36 is the lower end 16b of the column 12, it forms the bottom of the column 12 and the upper end 16a of the column 12 is the cover. The bed 14 then rests on the piston 36. The piston 36 and the bed 14 slide so as to make the upper surface of the bed 14 move closer to or further away from the cover of the column 12.

During chromatography, the bed 14 may expand or contract; consequently, the thickness of the bed 14 varies. When the bed 14 expands, the compression of the bed 14 between the two ends 16a, 16b may increase in such a way that the bed degrades; conversely, when the bed 14 contracts, the compaction of the bed is modified, the space between the bed and the end is increased and the chromatography device looses its effectiveness. The piston 36 then adapts the height of the column 12 according to the thickness of the bed 14. The piston makes it possible to protect the chromatographic bed 14 from any pressure greater than the mechanical strength of the bed 14, while ensuring the quality of the chromatography by the device.

To protect the bed 14, the chromatography device prevents the bed 14 from being compressed in contact with the two ends 16a, 16b of the column 12, one of the ends being the piston 36. To do this, the volume in the column 12 between the ends 16a, 16b is greater than the volume occupied by the bed 14. The fluid to be chromatographed that enters the column 12 then fills the difference in volume. Consequently, the fluid to be chromatographed, which flows in the column 12 through the bed 14, forms a layer 48; the layer is defined between one of the ends 16a, 16b and the upper surface of the bed 14. This allows the bed to be protected against the risk of being crushed and against mechanical stresses greater than those that the bed 14 can withstand.

The first probe 45 detects the upper surface of the bed 14. The first probe 45 is mounted on the end 16a which defines the layer 48, so as to detect the position of the surface of the bed 14 with respect to the upper end 16a of the column 12. When the piston 36 is the end 16a of the column 12 (FIG. 1), the first probe 45 is mounted on the piston 36. When the piston 36 is the end 16b of the column 12, the first probe 45 is, for example, mounted on the cover of the column 12. Depending on the detection of the surface of the bed 14 by the probe 45, the adjustment means 52 adjust the position of the piston 36. This has the advantage of allowing the position of the piston 36 with respect to the bed 14 to be automatically adjusted according to the detected movements of the latter. The probe 45 mounted on the end 16a of the column 12 also allows a simplified construction of the column 12, especially without a window for looking through the column 12.

In the embodiment shown in FIG. 1, the device 10 furthermore includes a second probe 46 for detecting the surface of the bed 14. The probe 46 is mounted on the end 16a of the column 12. Preferably, the probes 45 and 46 are the same so as to make it easier to process the information delivered by the probes. The probe 46 may be used to detect a malfunction of the first probe 45. It may also be used to supplement the detection of the surface of the bed 14 by the probe 45.

The probes 45, 46 may be mounted fixedly on the end 16a of the column. Fixed mounting has the advantage of simplifying the construction of the end 16a. Alternatively, the probes 45, 46 may be mounted so as to be able to move on the end 16a of the column 12; the probes 45, 46 are capable of undergoing oscillatory movements with respect to the end 16a. This has the advantage of allowing more accurate detection of the position of the surface of the bed and of allowing even better adjustment of the position of the piston with respect to the bed in order to draw on all its properties.

Advantageously, the probes 45, 46 project into the layer 48. This allows detection of the movements of the bed 14 to be improved. The probes 45, 46 may project by different amounts into the layer 48.

Detection of the surface of the bed by the probe may be effected by contact between the probes and the surface of the bed. However, advantageously the surface of the bed may be detected without any contact between the probes and the surface of the bed, the probe then being calibrated so as to detect the "proximity" of the surface of the bed. This has the advantage of avoiding any contact with the bed, and this increases its protection.

The nature of the probes 45, 46 will now be explained. In one embodiment, the probes 45, 46 are capacitive probes. These probes are electrically isolated from the medium surrounding them. They contain a capacitor whose capacitance changes with the dielectric constant of the medium around the probes. For example, as long as the probes 45, 46 are in contact with the fluid to be chromatographed, the value of the capacitance of the capacitor remains the same. When the bed expands, the probes 45, 46 are closer to the surface of the bed 14. Since the fluid has a dielectric constant different from that of the solid, the dielectric constant of the medium surrounding the probes 45, 46 changes. Detection of the surface of the bed by the probes may be effected by contact between the probes and the surface of the bed. However, advantageously the surface of the bed may be detected without any contact between the probes and the surface of the bed. This is because, as the surface of the bed is approached, the dielectric constant of the layer 48 changes, and this change is detected by the probes. This has the advantage of avoiding any contact with the bed, thereby increasing its protection. The change in the dielectric constant is detected by the probes 45, 46 and thus converted into a signal indicating the detection of the surface of the bed 14. The signal delivered by the probes 45, 46 is, for example, an on/off signal, that is to say, either the surface of the bed 14 is detected or it is not detected. Alternatively, the probes deliver continuous signals indicating the dielectric constant of the medium.

The adjustment means 52 comprise, for example, a regulator of the type with Proportional Integral, Proportional Differential or Proportional Integral Differential action. This type of regulator allows the position of the piston to be adjusted.

In FIG. 1, the displacement of the piston 36 in the column 12 is effected in the following manner. According to the embodiment depicted, the piston 36 is the end 16a. The device 10 includes a cylinder 22. The cylinder 22 has a moveable piston 24 connected to one end of a rod 26. The piston 24 defines two chamber 28 and 30 in the cylinder 22. The first chamber 28, or upper chamber, is defined between the piston 24 and the upper wall 32 of the cylinder 22. The second chamber 30, or lower chamber, is defined between the piston 24 and the lower wall 34 of the cylinder 22. The lower wall 34 marks the separation between the cylinder 22 and the column 12. The rod 26 connected to the piston 24 is in the lower chamber 30 and emerges in the column 12, passing through the lower wall 34 of the cylinder 22. Suitable seals will be used to seal between the chamber 30 and the column 12. The other end of the rod 26, which is in the column 12, is connected to the piston 36. A source 44 of hydraulic liquid supplies the cylinder 22 via line 38, 40. When the adjustment means 52 give the command to raise the piston 36, the pressure in the chamber 30 is made greater than the pressure in the chamber 28. When the adjustment means 52 give the command to lower the piston 36, the pressure in the chamber 28 is made greater than the pressure in the chamber 30.

According to another embodiment, the piston 36 is the end 16b and the cylinder 22 is positioned beneath the column 12.

The device according to the invention makes it possible to implement processes for separating at least two compounds of a fluid to be chromatographed and/or methods of adjusting the position of the piston in the device. These processes and methods make it possible to draw on all of the properties of the bed 14, while ensuring that the latter is protected from mechanical stresses greater than those that the bed 14 can withstand.

These processes and methods will now be described with reference to FIGS. 2 to 5.

Referring to FIG. 2, this shows an embodiment of the chromatography device comprising a probe 45 mounted on the piston 36 forming the end 16a of the column 12.

The initial positioning of the device is as follows. The bed 14 is deposited in the column 12, on the end 16b of the latter. The piston 36 is then introduced into the column 12. The piston 36 provided with the probe 45 is lowered until the probe 45 detects the surface of the bed 14, before the piston 36 comes into contact with the surface of the bed 14. A dead volume is defined between the piston 36 and the surface of the bed 14.

The process for separating at least two compounds of the fluid to be chromatographed in the device 10 is as follows. The fluid is conducted via a line 18 to the end 16a. The fluid fills the dead volume so as to form the layer 48 between the surface of the bed 14 and the piston 36. The fluid forming the layer 48 flows through the bed 14, while the layer 48 is replenished by the fluid coming from the line 18. After having passed through the bed 14, the fluid is collected at the end 16b of the column 12 and is removed via a line 20. The presence of the layer 48 prevents the piston 36 from coming into contact with the bed, thereby allowing it to be protected.

In another embodiment, the separation process is carried out in the following manner: the fluid is conducted via the line 20 to the end 16b of the column 12. It then passes through the bed 14 and the layer 48. Finally, the fluid is collected at the end 16a of the column 12 occupied by the piston 36 and then removed via the line 18. Because of the presence of the layer 48 between the surface of the bed 14 and the piston 36, the bed is protected from contact with the piston.

The method of adjusting the position of the piston 36 in the device 10 comprising the probe 45 fixed on the end 16a of the probe 12 is as follows. The piston then undergoes oscillatory movements allowing the probe to detect the surface of the bed. During the separation process, the fluid forming the layer 48 flows through the bed 14. The probe 45 delivers a signal indicating the position of the surface of the bed 14 at a predetermined frequency (the response time of the probe 45 may vary between a few milliseconds and a few hundreds of milliseconds). The frequency of measurement by the probe 45 is determined according to the characteristic time of movement of the bed 14. The frequency of movement of the bed may vary between a few minutes and a few hours. The frequency of measurement by the probe 45 is greater than the characteristic time of movement of the bed 14. Thus, the position of the piston is changed before the bed 14 comes into contact with the piston 36 and so as to maintain a constant gap (for example, between 1 and 20 mm and preferably between 2 and 7 mm) between the bed and the piston. If the probe detects the surface of the bed 14, for example when the bed expands, the adjustment means 52 give the command to raise the piston 36. If the probe 45 does not detect the surface of the bed 14, for example when the bed 14 contracts in the case of a head loss in the bed 14, the adjustment means 52 give the command to lower the piston 36. The chromatography device 10 continuously adapts the position of the piston to the movements of the bed 14. This allows the bed to be protected, while ensuring the quality of the fluid separation.

The method of adjustment may also be carried out with the device 10 by making the probe 45 oscillate. Throughout the duration of the flow of the fluid in the column and the separation of the fluid, the probe 45 undergoes oscillatory movements in order to detect the position of the surface of the bed 14 at a frequency greater than the characteristic time of movement of the bed 14 (characteristic time of movement of the bed: a few minutes to a few hours). The probe 45 undergoes a to-and-fro motion between an initial position and an extension position. The initial position is that furthest away from the surface of the bed; the extension position is that in which the probe is closest to the upper surface of the bed 14 in the layer 48. If during the oscillation the probe 45 detects the surface of the bed 14, a command is given by the adjustment means to raise the piston 36. If the surface of the bed 14 is not detected, a command is given by the adjustment means to lower the piston 36. Thus, when the bed has expanded, the piston is raised in order to protect the bed 14 from mechanical stresses greater than those that the bed 14 can withstand; if the bed 14 contracts, the piston is lowered in order to ensure optimum compaction of the bed and the quality of the chromatography. The advantage of the oscillations of the probe 45 is that the piston 36 slides after the probe has delivered information about the detection or non-detection of the surface of the bed 14. The protection of the bed and the quality of the separation are improved thereby.

Referring to FIG. 3, this figure shows an embodiment of the chromatography device comprising a probe 45 mounted on the end 16a of the column 12, the piston 36 being the lower end 16b of the column 12.

The initial positioning of the device 10 is as follows. The piston 36 is positioned in the column 12 so as to form the lower end 16b of the column 12. The bed 14 is deposited on the bottom of the column, against the piston 36, and then the column 12 is closed with the end 16a, a cover, for example, carrying the probe 45. The piston 36 and the bed 14 are then raised until the probe 45 detects the surface of the bed 14, before the end 16a comes into contact with the surface of the bed 14. A dead volume is defined between the piston 36 and the surface of the bed.

The fluid is introduced into and extracted from the column 12 via the respective lines 18 and 20, or vice versa.

The process for separating at least two compounds of the fluid to be chromatographed in the device 10 and the advantages are the same as those described in the case of FIG. 2.

The methods of adjustment with or without oscillation of the probe 45 are the same as those described in the case of FIG. 2. The difference is that when the probe 45 detects the surface of the bed 14, a command is given by the adjustment means 52 to lower the piston 36, taking the bed 14 with it; when the probe 45 does not detect the surface of the bed 14, a command is given by the adjustment means 52 to raise the piston 36, taking the bed 14 with it. In this embodiment, either the piston 36 or the probe undergoes the oscillatory movement with respect to the cover. It is also conceivable for the piston 36 and the probe 45 to undergo the oscillatory movement. The advantages are those described in the case of FIG. 2.

Referring to FIG. 4, this shows another embodiment of the chromatography device comprising two probes 45, 46 which are mounted on the piston 36 forming the end 16a of the column 12. Preferably, the probes 45, 46 project by different amounts into the layer 48; for example, the probe 45 projects further into the layer.

The initial positioning of the device is as follows. The bed 14 is deposited in the column 12, on the end 16b of the latter. The piston 36 is then introduced into the column 12. The piston 36 provided with the probes 45, 46 is lowered until the probe 45 detects the surface of the bed 14, before the piston 36 comes into contact with the surface of the bed 14. A dead volume is defined between the piston 36 and the surface of the bed 14.

The process for separating at least two compounds of the fluid to be chromatographed in the device 10 and the advantages are the same as those described in the case of FIG. 2.

The method of adjusting the position of the piston 36 in the device 10 comprising two probes 45, 46 fixed on the end 16a of the column 12 is the following. The piston undergoes oscillatory movements allowing the probes to detect the surface of the bed. During the separation process, the fluid forming the layer 48 flows through the bed 14. The probes 45, 46 deliver a signal indicating the position of the surface of the bed 14 at a predetermined frequency (the response time of the probes 45, 46 may vary between a few milliseconds and a few hundreds of milliseconds). The frequency of measurement by the probes 45, 46 is determined according to the characteristic time of movement of the bed 14. The frequency of movement of the bed may vary between a few minutes and a few hours. The frequency of measurement by the probes 45, 46 is greater than the characteristic time of movement of the bed 14. Thus, the position of the piston is changed before the bed 14 comes into contact with the piston 36 and so as to maintain a constant gap (for example between 1 and 20 mm preferably between 2 and 7 mm) between the bed and the piston. If the two probes 45, 46 detect the surface of the bed 14, for example when the bed expands, the adjustment means 52 give the command to raise the piston 36. If neither of the probes 45, 46 detects the surface of the bed 14, for example when the bed 14 contracts in the case of a head loss in the bed 14, the adjustment means 52 give the command to lower the piston 36. If the probe 45 detects the surface of the bed 14 but the probe 46 does not detect the surface of the bed 14, the adjustment means 52 do not give a command to move a piston. Making the probes 45, 46 project by different amounts allows the surface of the bed 14 to be flanked in a position in which the compaction is optimum for the quality of the separation and in which the bed is protected from pressures greater than the mechanical strength of the bed 14. The smaller the difference in the amounts by which the probes 45, 46 project, the more optimally the position of the surface of the bed 14 is defined. The chromatography device 10 continuously adapts the position of the piston to the movements of the bed 14. This allows the bed to be protected, while ensuring the quality of the fluid separation.

The method of adjustment-may also be carried out with the device 10 by making the probes 45, 46 oscillate. Throughout the duration of the flow of the fluid in the column and the separation of the fluid, the probes 45, 46 undergo oscillatory movements in order to detect the position of the surface of the bed 14 at a frequency greater than the characteristic time of movement of the bed 14 (characteristic time of movement of the bed: a few minutes to a few hours). The probes 45, 46 undergo a to-and-fro movement between an initial position and an extension position. The initial position is that furthest away from the surface of the bed; the extension position is that in which the probes are closest to the upper surface of the bed 14 in the layer 48. If during the oscillation the two probes 45, 46 detect the surface of the bed 14, for example when the bed expands, the adjustment means 52 give the command to raise the piston 36. If neither of the probes 45, 46 detects the surface of the bed 14, for example when the bed 14 contracts in the case of a head loss in the bed 14, the adjustment means 52 gives the command to lower the piston 36. If the probe 45 detects the surface of the bed 14 while the probe 46 does not detect the surface of the bed 13, the adjustment means 52 do not give the command to move the piston. Thus, when the bed has expanded, the piston is raised in order to protect the bed 14 against mechanical stresses greater than those that the bed 14 can withstand; if the bed 14 contracts, the piston is lowered in order to ensure optimum compaction of the bed and quality of the chromatography. The advantages obtained are the same as for the adjustment process without oscillation of the probes. The advantage of making the probes 45 and 46 oscillate is that a piston 36 slides after the probes have delivered information about the detection or non-detection of the surface of the bed 14. The protection of the bed and the quality of the separation are improved thereby.

Referring to FIG. 5, this shows another embodiment of the chromatography device comprising two probes 45, 46 mounted on the end 16a of the column 12, the piston 36 being the end 16b. Preferably, the probes 45, 46 project by different amounts into the layer 48; for example, the probe 45 projects further into the layer.

The initial positioning of the device 10 is as follows. The piston 36 is positioned in the column 12 so as to form the lower end 16b of the column 12. The bed 14 is deposited on the bottom of the column, against the piston 36, and then the column 12 is closed with the end 16a, a cover, for example, carrying the probes 45, 46. The piston 36 is then raised so that the probe 45 detects the surface of the bed 14, before the end 16a comes into contact with the surface of the bed 14. A dead volume is defined between the piston 36 and the surface of the bed 14.

The process for separating at least two compounds of the fluid to be chromatographed in the device 10 and the advantages are the same as those described in the case of FIG. 4.

The methods of adjustment with or without oscillation of the probes 45, 46 and the advantages are the same as those described in the case of FIG. 4. The difference is that when the probes 45, 46 detect the surface of the bed 14, a command is given by the adjustment means 52 to lower the piston 36, taking the bed 14 with it; when the probes 45, 46 do not detect the surface of the bed 14, a command is given by the adjustment means 52 to raise the piston 36, taking the bed 14 with it. In this embodiment, either the piston 36 or the probes undergo the oscillatory movement with respect to the end 16a. It is also conceivable for the piston 36 and the probes 45, 46 to undergo the oscillatory movement.

It is also possible to use more than two probes, the additional probes possibly being used to detect a malfunction of the primary probes.

The chromatography device according to the invention is advantageously used in a SMB (Simulated Moving Bed) process (U.S. Pat. No. 2,985,589, U.S. Pat. No. 3,291,726, U.S. Pat. No. 3,268,605 and U.S. Pat. No. 3,266,604 belonging to UOP, U.S. Pat. No. 5,578,215 and U.S. Pat. No. 5,578,216 belonging to IFP and NOVASEP, and EP 471 082 and EP 563 388 belonging to DAICEL) or in a VARICOL process (U.S. Pat. No. 6,136,198). Such processes employ a combination of these columns looped together.

Of course, the present invention is not limited to the embodiments described by way of example. Thus, the ends 16a and 16b of the column 12 may each be a piston.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosure of all applications, patents and publications, cited herein and of corresponding French Application No. 02 01 911, filed Feb. 15, 2002, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A chromatography device for separating at least two compounds, comprising
    a column intended to house, between its two ends, a chromatographic bed and a fluid to be chromatographed, a fluid layer being defined between a surface of the bed and one of the ends of the column;
    a piston sliding in the column, the piston being one of the ends of the column;
    at least a first probe for detecting the surface of the bed, the probe being mounted on the end of the column defining the layer; and
    means for adjusting the position of the piston according to the detection of the surface of the bed by the probe.

2. A device according to claim 1, wherein the piston is the lower end of the column.

3. A device according to claim 1, wherein the piston is the end defining the layer.

4. A device according to claim 3, further comprising a second probe for detecting the surface of the bed, the second probe being mounted on the end of the column defining the layer.

5. A device according to claim 2, further comprising a second probe for detecting the surface of the bed, the second probe being mounted on the end of the column defining the layer.

6. A device according to claim 1, wherein the probe is fixed on the end.

7. A device according to claim 1, wherein the probe is capable of undergoing oscillatory movements with respect to the end.

8. A device according to claim 1, wherein the probe projects into the layer.

9. A device according to claim 1, wherein the probe is a capacitive probe.

10. A device according to claim 1, further comprises a second probe for detecting the surface of the bed, the second probe being mounted on the end of the column defining the layer.

11. A device according to claim 1, wherein the first probe projects further into the layer than the second probe.

12. A combination of chromatography devices comprising a device according to claim 1 looped together with one or more further chromatography devices.

13. A combination of chromatography devices comprising two or more devices according to claim 1 looped together.

* * * * *